(12) United States Patent
Conway

(10) Patent No.: US 8,043,299 B2
(45) Date of Patent: Oct. 25, 2011

(54) INTERNAL BONE TRANSPORT

(76) Inventor: Janet Conway, Towson, MD (US)

( * ) Notice: Subject to any disclaimer, the term of this patent is extended or adjusted under 35 U.S.C. 154(b) by 335 days.

(21) Appl. No.: 12/221,061

(22) Filed: Jul. 30, 2008

(65) Prior Publication Data

US 2009/0062798 A1    Mar. 5, 2009

Related U.S. Application Data

(63) Continuation-in-part of application No. 11/593,999, filed on Nov. 6, 2006.

(51) Int. Cl.
*A61B 17/56* (2006.01)
*A61B 17/58* (2006.01)
*A61B 17/60* (2006.01)
*A61F 2/00* (2006.01)
*A61F 2/30* (2006.01)

(52) U.S. Cl. .......................................... 606/105; 606/62

(58) Field of Classification Search ............. 606/60, 606/62, 63, 251–262, 86 R, 90, 105
See application file for complete search history.

(56) References Cited

U.S. PATENT DOCUMENTS

| | | | |
|---|---|---|---|
| 3,790,507 A * | 2/1974 | Hodosh | 521/149 |
| 5,356,411 A | 10/1994 | Spievack | |
| 5,536,269 A * | 7/1996 | Spievack | 606/63 |
| 5,626,581 A | 5/1997 | Staehlin | |
| 5,704,938 A | 1/1998 | Staehlin | |
| 5,976,138 A * | 11/1999 | Baumgart et al. | 606/62 |
| 2005/0055025 A1 * | 3/2005 | Zacouto et al. | 606/72 |
| 2006/0004459 A1 * | 1/2006 | Hazebrouck et al. | 623/18.12 |

* cited by examiner

*Primary Examiner* — Thomas C. Barrett
*Assistant Examiner* — Sameh Boles
(74) *Attorney, Agent, or Firm* — Reed Smith LLP; Maryellen Feehery Hank

(57) ABSTRACT

An internal bone transport device and method for lengthen bone that, once surgically implanted will allow for a segment of bone to be transported along the length of the rod without changing the overall length of the rod. The segment from one bone end is transported to the other in a controlled fashion allowing for complete control of the rate of bone transport and adjusting this rate to the quality of the bone formation. The segment is moved either by the application of an externally applied magnetic force or by a fluid actuator in combination with a compression spring. It applies to patients in whom a segment of bone has been removed. This fully internal bone transport allows the bone transport to occur without any external fixation, thus eliminating the problems associated with pin tract infections and pain from the pins cutting through the soft tissue.

13 Claims, 5 Drawing Sheets

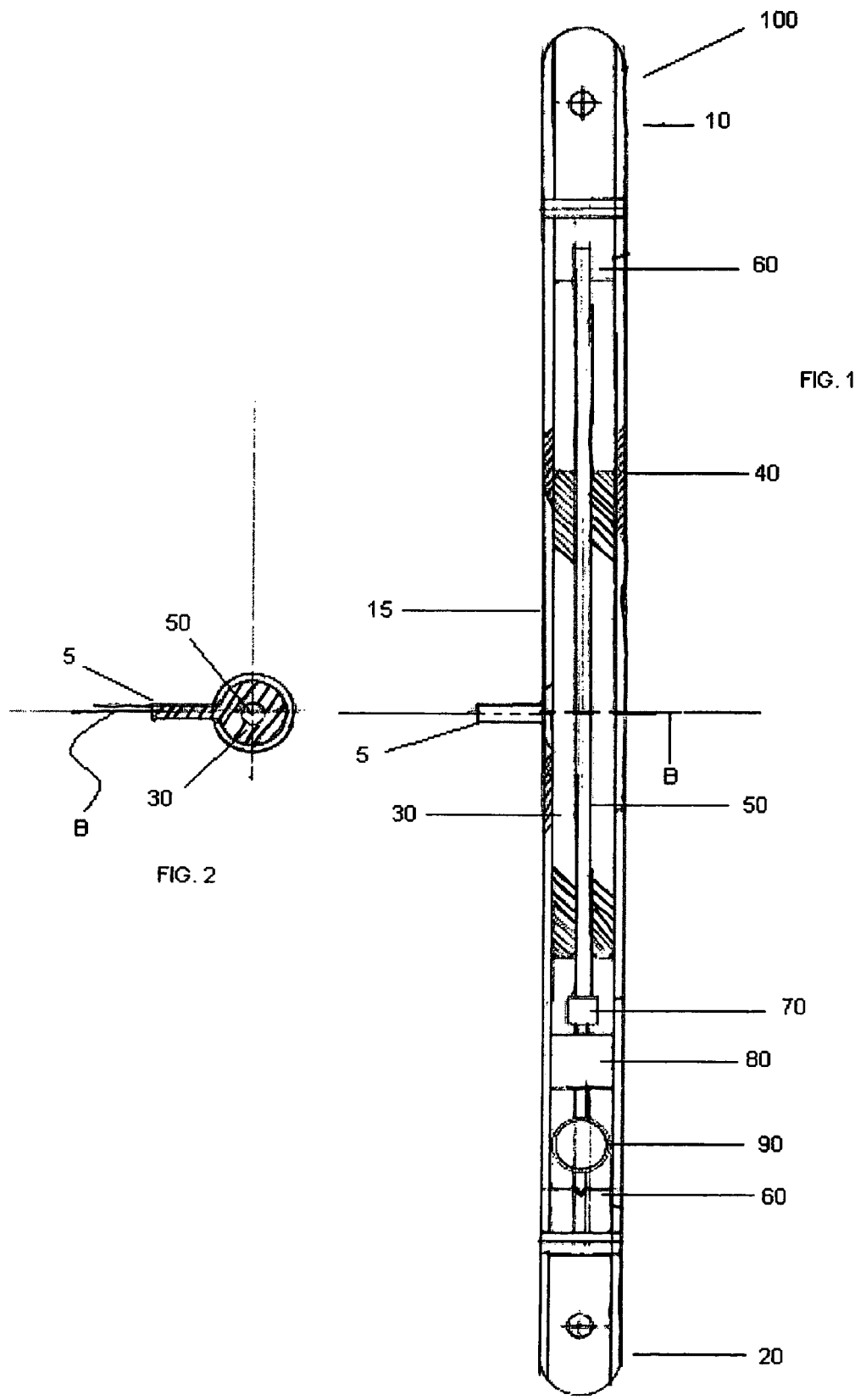

INTERNAL BONE TRANSPORT

CROSS-REFERENCE TO RELATED U.S. APPLICATION

This application is a continuation-in-part of U.S. patent application Ser. No. 11/593,999, filed on Nov. 6, 2006, the contents of which are hereby incorporated by reference.

TECHNICAL FIELD OF THE INVENTION

Generally, the present invention relates to an orthopedic device. More particularly, the present invention relates to an apparatus and methods for moving and lengthening bone.

BACKGROUND OF THE INVENTION

There are many means of stabilizing, moving, and lengthening bone. The need arises to stabilize, move and/or lengthen (collectively "lengthen") bone in a variety of situations, for example, to increase stature, even the length of a pair of limbs, and when a section of bone is removed following illness or trauma. Intercalary defects in long bones may occur as a result of trauma or after the resection of tumors or infection. With appropriate mechanical fixation, these defects may be managed by autogenous bone grafting, segmental allograft reconstruction, or reconstruction using endoprostheses. Autogenous bone grafting has the disadvantage of donor site morbidity including pain, increased blood loss, and surgical scarring. Furthermore, in the case of large defects it may be difficult or impossible to obtain an optimal volume of autogenous bone. While allografting eliminates the problem of adequate quantity, the incidence of complications such as infection, fracture, and non-union is increased. The risk of exposure to HIV or hepatitis is another concern.

In 1954 Ilizarov reported that mature bone can be elongated by gradual distraction of a fracture callus and called this process distraction osteogenesis. The application of this technique in the form of bone segment transport can obviate the need for open bone grafting in many large diaphyseal defects. However, transfixing wires used in this technique can cause significant complications including wire site infection, pain, and restricted joint motion due to the transfixation of tendons and muscles. These complications are particularly relevant when the Ilizarov device is applied to the femur.

In 1990 Brunner reported that distraction osteogenesis was achievable using intramedullary fixation in sheep tibiae. Brunner's method still relied on the use of an external fixator to provide the force necessary for bone transport. Brunner's work implied that transfixing wires used for internal fixation could potentially be eliminated.

Betz described the use of a telescoping intramedullary rod for distraction osteogenesis. With the Betz device, the patient apparently turned a small knob that protruded from the patient's hip in order to telescopically move the parts relative to one another.

Many bone lengthening devices have actuators or external fixators that penetrate the soft tissue of a patient and extend outside the body. For example, U.S. Pat. No. 5,429,638, which is incorporated herein by reference in its entirety, including any references cited therein, discloses a device for bone transport requiring a cable mechanism. The cable mechanism includes a cable that extends through the soft tissue to just under the skin. The bone is lengthened by a magnet that activates the actuator located under the skin, which in turn causes the implanted device to extend. Such a mechanism can cause infection and discomfort at the site where the cable penetrates the soft tissue.

There are several internal lengthening devices that have been patented, but none of the devices address the problem of transfixing a moving middle segment of bone along the length of a rod without changing the overall length of the rod. U.S. Patent Application No. 20040138663, which is incorporated herein by reference in its entirety, including any references cited therein, discloses a two-part telescopic intramedullary orthopedic device that connects two adjacent fractured or severed bones that can be moved toward or away from each other. The movement is actuated by an external magnetic field, such that one section may be moved axially in relation to the other section. U.S. Patent Application No. 20050261779, which is incorporated by reference in its entirety, including any references cited therein, discloses a rod-like prosthesis that can be expanded non-invasively by an externally applied magnetic field. The rod prosthesis is placed where a segment of bone was removed. The prosthesis is then extended.

Other patents and applications, such as U.S. Pat. Nos. 5,704,939, 6,336,929, and 6,796,984; French Patent No. 2726460; European Patent No. 0869473; and PCT Application No. 0164119, each of which is incorporated herein by reference in its entirety, including any references cited therein, disclose intramedullary devices that connect two bone segments and permit bone elongation between the two bone segments. However, none of them allow a third middle segment of bone to move in a bidirectional mode upon rotation of an external magnet.

Other patents, such as U.S. Pat. Nos. 5,356,411, 5,626,581, and 5,704,938, each of which is incorporated herein by reference in its entirety, including any references cited therein, disclose devices using fluid actuators having fluid containers which are filled by fluid reservoirs in order to cause one section of the device to be moved axially in relation to another section.

The pins, wires, cables, and other structures (herein collectively "pins") that penetrate the soft tissue in the prior art are sources of infection. This causes problems with joint contractures secondary to the transfixing of these soft tissues. The invention would allow for the middle segment of bone to be transported without the pins transversing the soft tissues, thus eliminating many post operative complications including pin tract infections, pain, and joint contractures. The pins dragging through the skin also causes large scar tracts to be formed which are unsightly and often require surgical excision. The invention eliminates this occurrence and thus the need for scar revision surgery.

SUMMARY OF THE INVENTION

The present invention provides a method of bone lengthening and a bone lengthening apparatus that does not have any pieces which break the skin or soft tissue and is located internally with the sole exception of an actuator which generates a magnetic force outside the body and is applied through the skin and soft tissue without breaking the skin or soft tissue. This invention utilizes three or more bones, including a first and a second bone which ends are not connected and at least one middle bone which is placed between the ends of the first and second bones (in order to allow osteogenesis to occur between the bone segments in the process of achieving the desired bone length) and moves on an axis which runs through the first, second, and middle bones.

Bone in this specification includes, but is not limited to bones and/or bone segments, which may be made of bone materials, natural materials, synthetic materials, and mixtures thereof.

According to an embodiment of the present invention, the internal bone transport device has an external rod of substantially fixed length (also referred to as "substantially fixed length rod") with two ends, each of which may be coupled, attached, or affixed to a different bone. The internal bone transport has at least one moveable member that is capable of moving along the internal rod. The moveable member is coupled to a bone and moved along the length of the external rod by an external magnet that rotates a magnetic material housed within the external rod. The moveable member has a projecting member for coupling the middle bone to the moveable member. An internal rod (also referred to as "longitudinally rotatable rod"), which may be threaded, is housed within the external rod and may optionally be coupled with a gearbox. The gearbox is coupled with the magnetic material such that when an external magnetic field is created, the magnetic material is rotated. The rotation of the magnetic material in turn causes the gearbox to rotate the coupled internal rod. The rotation of the internal rod causes the moveable member to move lengthwise along the internal rod and substantially parallel to the external rod. Rotation of the internal rod does not cause the moveable member to rotate, but rather causes the moveable member to move in a substantially lengthwise direction within the external rod. The internal bone transport permits bidirectional movement of a bone lengthwise along the external rod.

According to an embodiment of the invention, the internal bone transport device has a hydraulic or fluid actuator in combination with a compression or torsional spring instead of a magnetic actuator. As in the previously described embodiments, the internal bone transport device of the fluid actuator embodiment has a substantially fixed length rod with two ends; each end may be coupled, attached, or affixed to a different bone. The internal bone transport has at least one moveable member that is capable of moving along the internal rod. The moveable member is coupled to a bone and moved along the length of the substantially fixed length rod. One end of a compression spring is attached, or affixed to one end of the substantially fixed length rod, while the other end of the compression spring is attached, or affixed to the moveable member. A sealed variable volume fluid container such as, without limitation, a sealed silicone bladder is positioned between the other end of the substantially fixed length rod and the moveable member. A flexible conduit has one end fluidly coupled to the fluid container, while the other end is fluidly coupled to a one-way valve. The fluid container and flexible conduit are filled with a fluid compatible with the body such as saline. An actuator is positioned outside the device and may be positioned outside the body operable to control the one-way valve. The actuator is preferably a remote control device such as a magnetic, electromagnetic, radio frequency, and mixtures thereof controlled device. Movement of the moveable member is caused by the actuator opening the one-way valve to allow fluid to escape the variable volume fluid container and flexible conduit. This decreases the volume of fluid in the fluid container, thus, allowing the compression spring to act against the moveable member from the other side to cause the moveable member to move in a substantially lengthwise direction within the external rod.

According to an embodiment of the invention, two moveable members are used to transport a pair of bone segments towards one another. The internal bone transport device has a variable volume fluid container between the pair of moveable members. The device further includes a pair of compression springs such that each spring is attached, or affixed, at one end to a moveable member and at the other end to one end of the external rod. Upon actuation by an actuator, fluid is released from the variable-volume fluid container thus, allowing the compression springs to expand. The expansion of the compression springs transports each moveable member along the internal rods towards the other moveable member. Thus, a pair of bone segments is able to be transported at the same time.

According to an embodiment of the invention, the internal bone transport device may include an adaptor piece to provide a bend or curve angled at 15° from a vertical axis in order to accommodate the proximal tibial curve and for ease of insertion. The adaptor piece has an externally-threaded end for attachment to a corresponding internally-threaded end located on one of the ends of the external rod.

BRIEF DESCRIPTION OF THE DRAWINGS

The internal bone transport of the present invention, is best understood with reference to the following detailed description of the invention and the drawings in which:

FIG. 1 is a schematic view of an embodiment of an internal bone transport device;

FIG. 2 is a cross-sectional view of an embodiment of an internal bone transport device;

DETAILED DESCRIPTION

Figure 3:
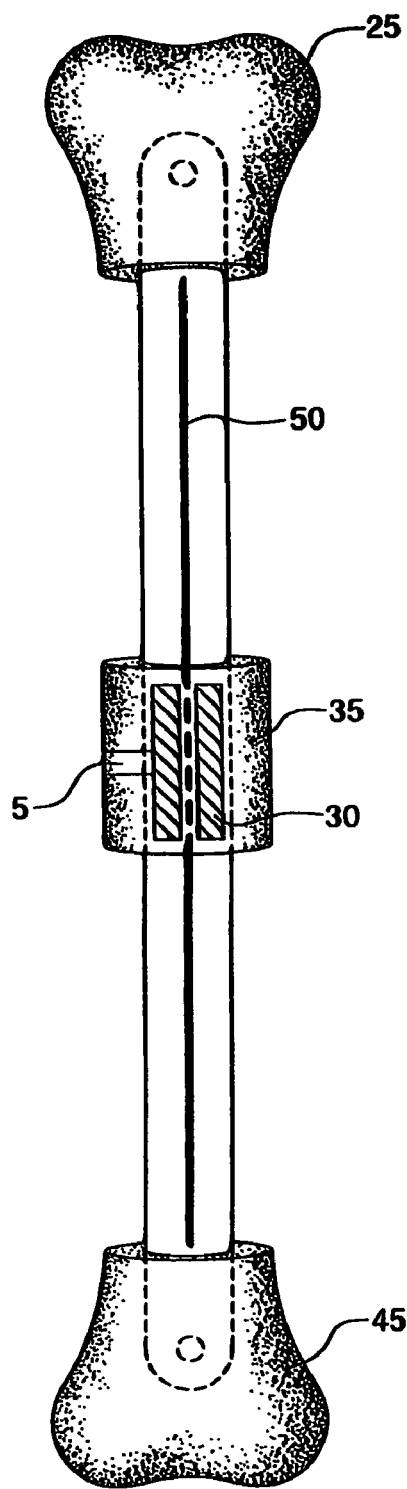
FIG. 3 is a schematic view of an embodiment of an internal bone transport device illustrating the device coupled with bone segments.

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

According to an embodiment illustrated in FIG. 1, the internal bone transport (100) has an external rod or tube (herein collectively "external rod") (40) having a first end (10) and second end (20). The first end (10) and second end (20) are capable of being coupled with a bone. The first end

(10) and second end (20) may be coupled with a bone by methods known in the art, including but not limited to screws, pins, cement, and/or glue. Preferably, the first end (10) and the second end (20) may be coupled with a first bone (25) and a second bone (45), respectively, by a screw, more preferably by two or more screws.

According to an embodiment, the first end (10) and second end (20) of the external rod (40) may be sealed using a cap, plug, cork, stopper, or other seal known in the art (collectively "cap"). The first end (10) and second end (20) of the external rod (40) may be implanted into the intramedullary space of a first bone (25) and a second bone (45). The first end (10) and second end (20) of the external rod (40) may also be coupled with the exterior or any part of a first bone (25) and/or second bone (45). A moveable member (30) is capable of being coupled with a bone segment, which may be made of bone material, natural material, synthetic material, or mixtures thereof and is configured to move lengthwise along the internal rod (50). According to an embodiment, one or more, preferably one or two or three moveable member(s) (30) may be used with the present invention to move multiple bone segments (preferably one moveable member (30) to one bone segment). The multiple bone segments may be moved along an external rod (40) in the same or different direction, such as but not limited to toward each other to achieve bone regeneration.

According to an embodiment, the moveable member (30) has at least one removable projecting member (5). The projecting member (5) may be transfixed to a middle bone (35) and optionally the moveable member (30). The projecting member (5) may be inserted from outside the internal bone transport device (100) through a slot(s) (15) in the external rod (40), into the middle bone (35), and into the moveable member (30), but not the internal rod (50). According to an embodiment, the projecting member (5) may be the fastening mechanism, such as a screw or pin, preferably a screw. The moveable member (30) is coupled with an internal rod (50), which functions as a lead screw. The internal rod (50) is housed within the external rod (40) and may be coupled at each end with a bearing (60) that supports and guides the rotation of the internal rod (50). The internal rod (50) is attached to a coupling (70), which couples the internal rod (50) with an optional gearbox (80). The gearbox (80) is coupled with a magnetic material (90). The internal rod (50) is capable of being rotated by the gearbox (80) by the rotation of the magnetic material (90). Rotation of the internal rod (50) does not cause the moveable member (30) to rotate, but rather the rotation of the internal rod (50) causes the moveable member (30) to move substantially lengthwise along the internal rod (50). The magnetic material (90) may be a magnet or other material responsive to a magnetic field and/or a radio frequency, or an electromagnet, preferably a magnet or other material responsive to a magnetic field.

According to an embodiment, the middle bone (35) may begin by being located toward one end of the initial opening where the natural process of "knitting" would be initiated. The natural process of "knitting" or bone formation is called distraction osteogenesis. This middle bone (35) may be physically fastened to a moveable member (30). When caused to do so by subjection, or coupling the internal bone transport device (100) to a strong magnetic field from outside the body, the device (100) would motivate the middle bone (35) to be transported across the opening between the first bone (25) and the second bone (45) to enable healing of the entire opening. This movement would be done gradually and precisely, thereby providing a sufficiently large force to reliably displace the segment of bone against the resistance of natural materials produced by the body in the process of "knitting" the bone back together.

According to an embodiment, the middle bone (35) may be moved up or down along the external rod (40) to achieve proper regeneration of bone. The quality of bone regeneration during the "knitting" process may be altered by increasing or slowing down the rate of bone movement along the external rod (40). Further, bidirectional movement of the middle bone (35) coupled with the moveable member (30) may also simulate load/weight bearing characteristics to further aid and/or improve the quality of the bone regeneration and/or the rate of regeneration.

According to an embodiment illustrated in FIG. 2, a cross-sectional view of the internal bone transport (100) along axis B is set forth. The cross-sectional view shows the projecting member (5) coupled to the internal rod (50) and extending out from the external rod (40) through the slot(s) (15).

According to an embodiment, the external rod (40) may be made of titanium, medical grade titanium, stainless steel, surgical grade stainless steel, cobalt chromium, or any other material suitable for implant devices. Preferably, the external rod (40) is made of surgical grade stainless steel. The external rod (40) may be of any length depending upon the bone to be lengthened or the length of the original bone. Preferably, the external rod (40) is sufficiently longer than the space between the first bone (25) and the second bone (45) so that the external rod (40) may be fastened to each. According to an embodiment, the length of the external rod (40) will vary depending upon the size, length, and/or shape of the bone to be regenerated and/or lengthened. For example, without limitations, the length of an external rod (40) used with a femur may range from about 25 cm to about 50 cm in length; for a tibia the range may be from about 20 cm to about 40 cm; for a humerus the range may be from about 15 cm to about 30 cm; and for a forearm the range may be from about 10 cm to about 20 cm. Further, the external rod (40) may have any diameter that is suitable for implantation. For example, without limitations, an external rod (40) for a femur may have an external diameter between about 10 mm and about 15 mm; for a tibia a diameter between about 9 mm and about 14 mm; for a humerus a diameter between about 7 mm and about 9 mm; and for a forearm a diameter between about 4 mm and about 6 mm. The external rod (40) may be of any shape necessary to lengthen, strengthen, or regenerate the missing bone, such as for example substantially round, oval, or a shape with a multiple number of sides, such as an octagon. Preferably, the shape of the external rod (40) is substantially a cylinder.

According to an embodiment, the external rod (40) may also be of a length equivalent to the distance from the hip to the ankle of a patient. An internal bone transport device (100) of such a length may be necessary in such situations as when a knee joint cannot be replaced (referred in the art as knee fusion) or there is massive bone loss.

According to an embodiment, a portion or the entire external rod (40) may have a bend or curve. The bend or curve may be necessary to ease implantation and/or accommodate the fit of the external rod (40) within the bone to be regenerated or lengthened. For example, the proximal end of an external rod (40) that may be placed in a tibia may have an angle of about 15° for ease of insertion. The angle may occur anywhere along the length of the external rod (40) and may be made suitable to each bone to be regenerated or lengthened. According to an embodiment, the external rod (40) may also be substantially straight.

According to an embodiment, the internal bone transport system (100) may include multiple pieces that may be assembled prior to, after, and/or during implantation.

The bones that may be lengthened in this method and apparatus include, but are not limited to the femur, tibia, fibula, humerus, radius, ulna, mandible, and/or phalanges.

According to an embodiment, any part of the internal bone transport (100), including, but not limited to the external rod (40), the internal rod (50), and the moveable member (30), and the magnetic material (90); as well as any part of the bone, including but not limited to, the first bone (25), the second bone (45), and/or the middle bone (35) may have one or more coatings. The coatings may include, but are not limited to an antibiotic, silver, polymer, bone morphogenic protein, parylene, any inert substance that prevents corrosion (wherein said preventing may include without limitation resisting), and/or any combination thereof. Such a coating may provide benefits such as, but not limited to an antibacterial effect; to ease insertion and/or implantation of the device; prevent corrosion; and/or promote bone regeneration.

According to an embodiment, the external rod (40) may be hollow or substantially hollow to house the components of the device. The external rod (40) may also have a slot(s) (15) through which the projecting member (5) is attached to the middle bone (35). The slot(s) (15) runs substantially along the longitudinal axis of the external rod. The slot(s) (15) shall be of sufficient length to move the middle bone (35) the required distance to make the desired healed bone length. The slot(s) (15) may be of any length and width, preferably having a length of about 15 cm to about 20 cm and having a width of about 3 mm to about 6 mm. The slot(s) (15) is designed to fit the needs of the patient, such as for example, the amount of bone regeneration necessary to elongate the bone to its normal length. The slot(s) (15) is also designed to fit the projecting member (5) used to couple the middle bone (35) with the moveable member (30).

According to an embodiment, the external rod (40) may have more than one slot(s) (15) and be located at various lengthwise positions along the external rod (40) so that it may be used for such things as, but not limited to different dimensions of bone and/or increased stability. The external rod (40) may also or alternatively have more than one slot(s) (15) distributed around the external rod (40) at various angles with respect to each other. For example a first slot(s) (15) may be on opposite sides of the external rod (40) (at a 180° angle). Preferably, a first slot(s) (15) is perpendicular (at a 90° angle) to a second slot(s) (15).

According to an embodiment, an absorbable, biodegradable material, such as but not limited to gel foam, may be inserted into the slot(s) (15) to prevent occlusion of the slot(s) (15) upon insertion into the bone. Using such material prevents any substance and/or material, foreign or native to a patient's body, from entering the internal bone transport (100) through a slot(s) (15). The material is capable of melting and/or being absorbed after implantation of the device as a result of being in contact with internal body fluids and/or temperatures and thus permitting the opening of the slot(s) (15).

According to an embodiment, the projecting member (5) may be a screw, pin, bone cement, calcium phosphate, resorbable material, and/or any other suitable mechanism known in the art, preferably a screw. According to an embodiment, more than one projecting member (5) may be used with the present invention. Preferably, one projecting member (5) is used with each slot(s) (15) that may be incorporated into the external rod (40) to secure a middle bone (35) to the moveable member (30). The projecting member (5) may be of any shape and/or size to accommodate the needs of the patient and/or the requirements for movement of bone.

Figure 4:
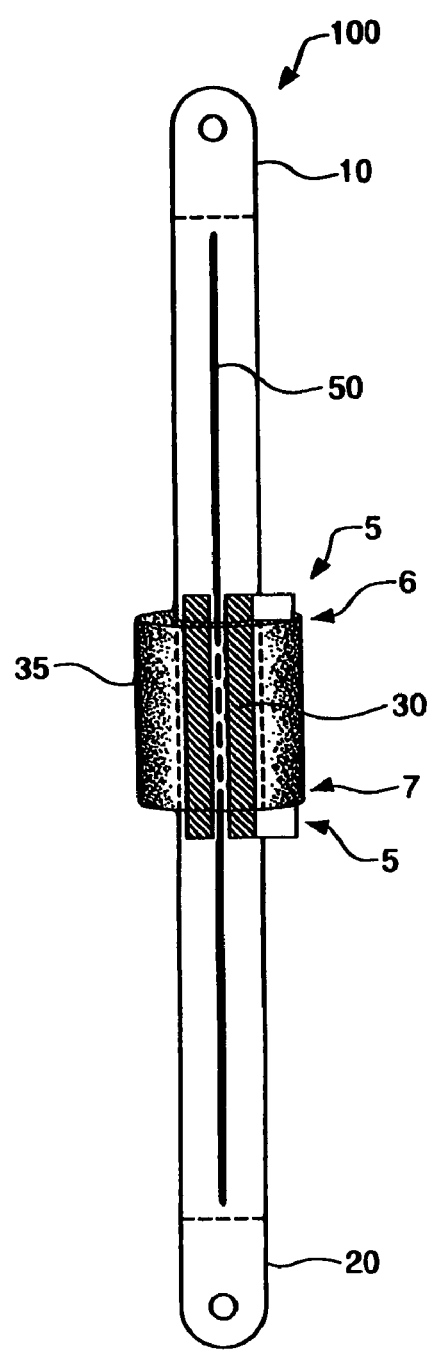
FIG. 4. is a schematic view of an embodiment of an internal bone transport device illustrating the projecting member above and below a middle bone.

Referring to FIG. 3, according to an embodiment, the projecting member (5) may be transfixed to the middle bone (35) by way of a mechanism that transverses the middle bone (35). Referring to FIG. 4, according to another embodiment, a projecting member (5) may be located just above the proximal end (6) of the middle bone (35) and just below the distal end (7) of the middle bone (35) and not penetrate the middle bone (35), but penetrate the moveable member (30). Further, according to additional embodiments, the projecting member (5) may be in any configuration that permits the middle bone (35) to be coupled with the moveable member (30). Further, any means known in the art may be used to couple the middle bone (35) with the moveable member (30) via the projecting member (5).

According to an embodiment, the projecting member (5) may penetrate through the middle bone (35) into the moveable member (30) at a sufficient depth to secure the middle bone (35) with the moveable member (30) but not penetrate the internal rod (50), preferably between about 2 mm and about 5 mm. According to an embodiment, the projecting member (5) may penetrate the middle bone (35) and secure into the moveable member (30) substantially perpendicular to the moveable member (30). In one embodiment, the projecting member (5) may penetrate the middle bone (35) and moveable member (30) not along part of the diameter of the moveable member (30), but along a section in the substantially same plane as the diameter. According to an embodiment, the projecting member (5) may penetrate the middle bone (35) and couple with the moveable member (30) at any angle with respect to the moveable member (30).

According to an embodiment, the projecting member (5) may be coated with an antibiotic, silver, a polymer, bone morphogenic protein, parylene, any inert coating that prevents corrosion (wherein said preventing may include without limitation resisting), and/or any combination thereof. Bone morphogenic protein may also be used on or around any sites of attachment of the internal bone transport (100) to bone and/or points of contact between the internal bone transport (100) and bone.

According to an embodiment, the projecting member (5) may be made of titanium, medical grade titanium, stainless steel, surgical grade stainless steel, cobalt chromium, or any other material suitable for implant devices. Preferably, the projecting member (5) is made of surgical grade stainless steel.

According to an embodiment, the moveable member (30) may be made of titanium, medical grade titanium, stainless steel, surgical grade stainless steel, cobalt chromium, or any other material suitable for implant devices. Preferably, the moveable member (30) is made of surgical grade stainless steel.

According to an embodiment, the moveable member (30) may have a substantially hollow center to receive the internal rod (50). Further, the hollow center of the moveable member (30) may be threaded. The moveable member (30) is coupled with the internal rod (50) by the threading of the moveable member (30) and the internal rod (50). The moveable member (30) is located peripherally around at least a part of the internal rod (50). As used in this specification, "peripherally" includes substantially peripherally. According to an embodiment, the internal rod (50) acts like a screw and the moveable member (30) acts like a nut, such that the threading of both enable the moveable member (30) to move along the length of the internal rod (50). Preferably, the internal rod (50) rotates and the moveable member (30) does not substantially rotate.

The moveable member (30) is capable of moving bidirectionally. The moveable member (30) may be of a length to maintain a seal along the slot(s) (15) in the external rod (40) as the moveable member (30) is moved along the internal rod (50) to prevent movement/passage of body fluids/material or other materials into or out of the external rod (40) through the slot(s) (15).

According to an embodiment, the moveable member (30) that is housed within the external rod (40) may be located so that the center of the diameter of the moveable member (30) is substantially the same as the center of the diameter of the external rod (40). The moveable member's (30) center of diameter may also be located offset in any direction from the center of the diameter of the external rod (40). As referred to herein, "diameter" means the diameter of a circle or the longest section from one edge to another edge without going outside the shape and through the center of the shape, wherein the shape is not a circle.

According to an embodiment, the internal rod (50) that is at least partially located within the moveable member (30) may be located so that the center of the diameter of the moveable member (30) being substantially the same as the center of the diameter of the internal rod (50). The internal rod's (50) center of diameter may also be located offset in any direction from the center of the diameter of the moveable member (30).

According to an embodiment, the internal rod (50) may be made of titanium, medical grade titanium, stainless steel, surgical grade stainless steel, cobalt chromium, or any other material suitable for implant devices. Preferably, the internal rod (50) is made of surgical grade stainless steel. The thread of the internal rod (50) may have any pitch necessary to achieve the desired results. Preferably, the pitch of the thread would be approximately 80 threads per inch (approximately a pitch of 0.0125 inches). The internal rod (50) may be of various lengths and widths based upon the length and width of the external rod (40) and/or the required movement of the internal rod (50).

According to an embodiment, the internal rod (50) may have a length of between about 20 cm and about 50 cm for a femur; between about 15 cm and about 40 cm for a tibia; between about 10 cm and about 30 cm for a humerus; and between about 5 cm and about 20 cm for a forearm. The internal rod (50) may have of any diameter suitable to work within the external rod (40) and/or meet the demands/requirements for a particular bone to be lengthened, such as but not limited to between about 3 mm and about 15 mm, preferably between about 4 mm and about 7 mm.

According to an embodiment, the internal rod (50) that is housed within the external rod (40) may be located so that the center of the diameter of the external rod (40) being substantially the same as the center of the diameter of the internal rod (50). The internal rod's (50) center of diameter may also be offset in any direction from the center of the diameter of the external rod (40).

According to an embodiment, the gearbox (80) permits a rotation ratio of 10-20:1, wherein for every 10-20 rotations of the magnetic material (90), the internal rod (50) rotates moving the moveable member (30) approximately 1 millimeter. As is known in the art, daily or more frequent movements which are small increments of the bone to be healed, work better than less frequent, large movements of the bone to be healed. However, such large movements may be made based upon the needs of the patient. According to an embodiment, the bone segment coupled with the moveable member (30) may be moved about 1 mm per day, preferably about ¼ mm four times a day. According to another embodiment, the gearbox (80) is optional, such that rotation of the magnetic material (90) rotates the internal rod (50) thereby resulting in the moveable member (30) moving lengthwise along the internal rod (50) in a one to one (1:1) ratio with the internal rod (50). According to an embodiment, the optional gearbox (80) may be made or adjusted to generate any movement ratio that is required by the needs of the patient.

According to an embodiment, the magnetic material (90) may be a magnet or other material responsive to a magnetic field or radio frequency, such as but not limited to electromagnet, rare earth magnets, ceramic, ferrites, alnico (aluminum nickel cobalt alloy), neodymium, iron, and/or iron alloys. The magnetic material (90) is rotated by an external actuator. According to an embodiment, the external actuator may include but is not limited to rare earth magnets and/or electromagnets.

According to an embodiment, the first end (10) and the second end (20) of the external rod (40) may include end caps that seal each end of the external rod (40). The end caps may be made of the same material as that of the external rod (40). The first end (10) and the second end (20) of the external rod may be a continuous part of the external rod (40) or may be separate pieces capable of being removed from the external rod (40).

According to an embodiment, varying the thread pitch of the internal rod (50) and/or the type, strength, size, orientation of the magnetic material (90) housed within the hollow of the external rod (40) will adjust the pounds of linear thrust created and delivered to moveable member (30) to move the middle bone (35). According to an embodiment, between about 50 and about 100 pounds of linear force may be exerted, preferably between about 60 and 90 pounds of linear force, more preferably about 60 pounds. According to an embodiment, the force necessary to move the middle bone (35) may depend on such factors as the distance the bone must be moved, the type of bone, the effects of soft tissue around the bone, and whether the bone to be lengthen is that of a child, adolescent, or adult.

Figure 5:
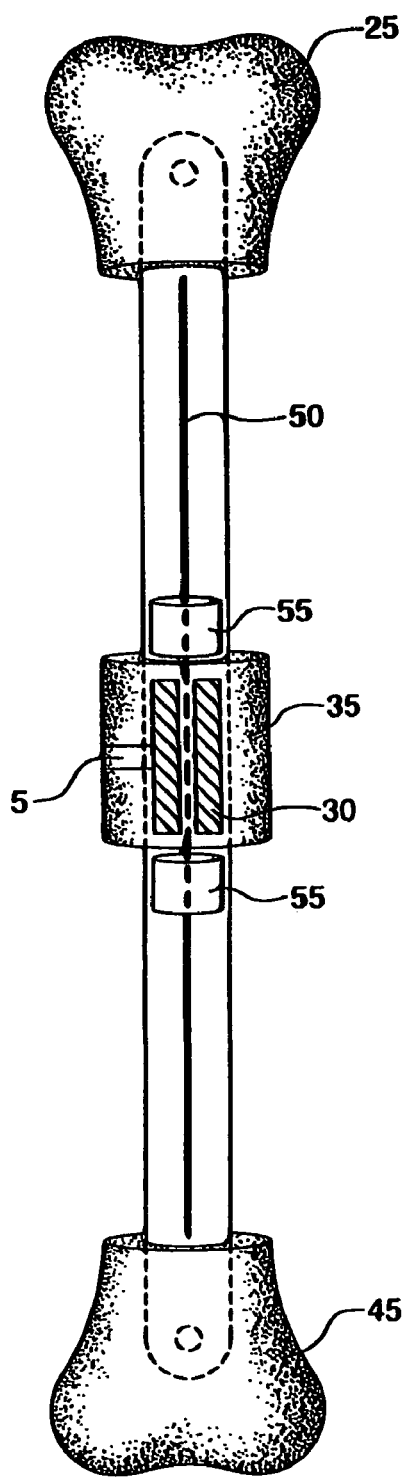
FIG. 5. is a schematic view of an embodiment of an internal bone transport device illustrating a nut(s) used to move a middle bone.

According to another embodiment, referring to FIG. 5, the internal rod (50) may be secured within the hollow of the external rod (40) such that the internal rod (50) is incapable of being rotated. In this embodiment, the moveable member (30) is located peripherally around at least a part of the internal rod (50). The hollow of the moveable member (30) may be substantially smooth. Above and/or below the moveable member (30) is a nut(s) (55) that is threaded. The nut(s) (55) is located peripherally around at least a part of the internal rod (50) such that the threads of the nut(s) (55) receive the threads of the internal rod (50). The nut(s) (55) rotates while the internal rod (50) is substantially stationary. When the nut(s) (55) is rotated, the moveable member (30) moves substantially up and down the internal rod (50) and substantially does not rotate.

According to an embodiment, the nut(s) (55) may be made of a material that has magnetic properties, including but not limited to an electromagnet, rare earth magnets, ceramic, ferrites, alnico (aluminum nickel cobalt alloy), neodymium, iron, and/or iron alloys. The nut(s) (55) may also be made of titanium, medical grade titanium, stainless steel, surgical grade stainless steel, cobalt chromium, or any other material suitable for implant devices and have a material that has magnetic properties coupled with the nut(s) (55), including, but not limited to electromagnet, rare earth magnets, ceramic, ferrites, alnico (aluminum nickel cobalt alloy), neodymium, iron, and/or iron alloys.

According to an embodiment, the nut(s) (55) is capable of being rotated by an external force generated by an external actuator. The external force used to move the moveable member (30) via the movement of the nut(s) (55) and/or internal rod (50) may be applied from outside or externally from a patient's body and/or body part without breaking the skin or soft tissue. Rotation of the nut(s) (55) causes the moveable member (30) to move along the internal rod (50).

According to an embodiment, the nut(s) (55) may be located anywhere along the length of the internal rod (50) and when two nut(s) (55) are used one nut(s) (55) is located above the moveable member (30) and one is located below the moveable member (30). According to an embodiment, when more than one nut(s) (55) is used, the nut(s) (55) may be moved at the same time or may be moved separately depending upon the desired movement of the moveable member (30).

According to another embodiment, the nut(s) (55) may be secured to the internal rod (50) such that rotation of the nut(s) (55) causes rotation of the internal rod (50) and thereby causes movement of a threaded moveable member (30) substantially up and down within the longitudinal plane of the external rod (40) (wherein the threads are in the hollow of the moveable member (30)) along the internal rod (50). The nut(s) (55) may be located anywhere along the length of the internal rod (50).

Figure 6:
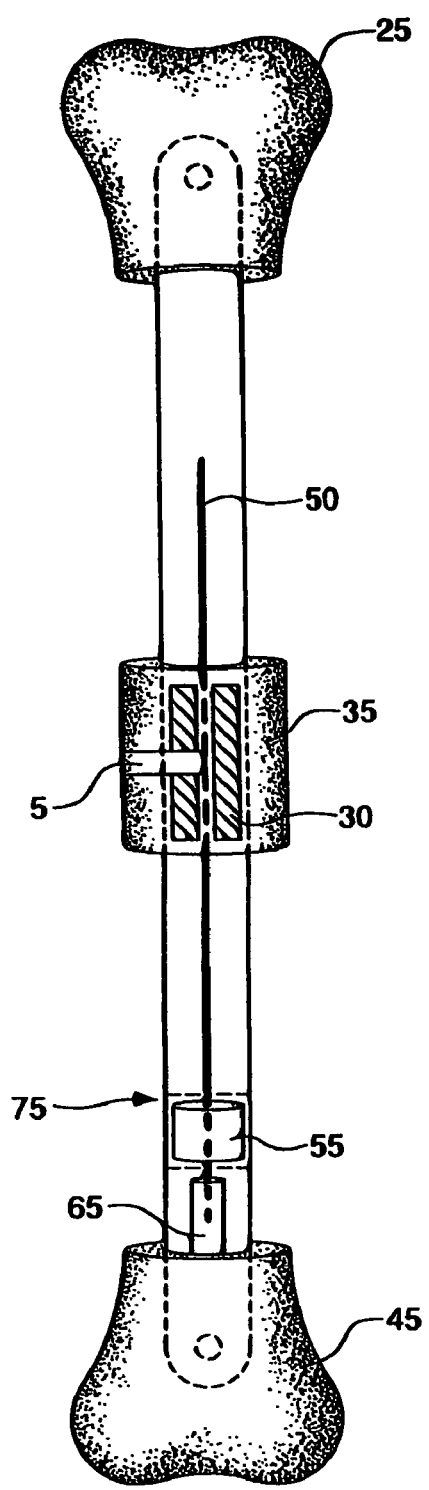
FIG. 6 is a schematic view of an embodiment of an internal bone transport device illustrating an internal rod coupled with a nut to move a middle bone and an optional receiving tube

According to another embodiment, referring to FIG. 6, the internal rod (50) may have a shorter length than the external rod (40) to permit movement of the internal rod (50) substantially up and down within the longitudinal plane of the external rod (40). In this embodiment, the projecting member (5) may penetrate the middle bone (35) and the moveable member (30) through slot(s) (15) and be secured to the internal rod (40). Such an orientation may result in the moveable member (30), the middle bone (35), and the internal rod (50) to move as one unit.

According to an alternative embodiment, the projecting member (5) may penetrate the middle bone (35) and be secured directly to the internal rod (50) through a slot(s) (15) without the use of the moveable member (30). Further, in this embodiment, a nut(s) (55) is housed within a portion of the hollow of the external rod (40) such that the nut(s) (55) is capable of freely rotating, but incapable of sliding up or down along the longitudinal plane of the external rod (40). Rotation of the nut(s) (55) causes the internal rod (50) which is coupled with the middle bone (35) to move the middle bone (35) along the external rod (40).

According to an embodiment, there may be a bearing interface (75) between such locations as, but not limited to the nut(s) (55) and the moveable member (30); the nut and any portion of the internal bone transport device (100); or the internal rod (50) or a portion thereof and the external rod or a portion thereof to allow free rotational and/or longitudinal movement of the portion of the device that requires free movement. The bearing interface (75) may be, but is not limited to a polymer, any substance with a low friction interface, and/or any bearing interface (75) known in the art.

According to an embodiment, the external rod (40) may optionally house one or more receiving tube(s) and/or bushing (collectively "receiving tube(s)") (65) to guide the movement of the internal rod (50) when the nut(s) (55) is rotated to move the unit that may include the internal rod (50), the middle bone (35), and the optional moveable member (30) along the longitudinal plane of the hollow of the external rod (40). The receiving tube(s) (65) may be of any length and/or size to guide and/or receive the internal rod (50). The receiving tube(s) (65) may also have a bearing interface (75), such as but not limited to a polymer surface, any substance with a low friction interface, and/or any other bearing interface (75) known in the art.

According to an embodiment, where an optional receiving tube(s) (65) is not used, the moveable member (30) and internal rod (50) may substantially fill the inner diameter of the external rod (50). There may also be a bearing interface (75) between the external rod (50) and moveable member (30) to allow longitudinal movement of the moveable member (30) along the interior of the external rod (40).

According to an embodiment, where an optional gearbox (80) may or may not used, the rotation of the nut(s) (55) and/or the internal rod (50) that causes the moveable member (30) to move along the internal rod (50) may have a pitch of about 1 mm such that one full turn of the nut(s) (55) and/or internal rod (50) results in the middle bone (35) moving about 1 mm along the length of the external rod (40). For example, but in no way limiting, the pitch of the threads of the nut(s) (55) and/or internal rod (50) may be about ½s of an inch.

According to an embodiment, use of the invention will now be described. The first end (10) and the second end (20) of the external rod (40) attach to the first bone (25) and the second bone (45) maintaining the overall length following the removal of a segment of bone for various reasons including without limitation trauma, infection, or disease. One of the remaining bones is then cut surgically and this portion is transfixed to the moveable member (30) between the end bones, which is in turn coupled with the internal rod (50). The cut segment is transported from a first bone (25) to a second bone (45), or vice versa at a rate that allows for optimal distraction osteogenesis or new bone formation. According to an embodiment, multiple moveable members (30) may be used, such that multiple bone segments may be moved to regenerate bone. The moveable member(s) (30) may move in the same direction with respect to each other, away from each other, or towards each other. Bone growth rate is affected by age, lifestyle, whether the patient smokes, and other factors.

According to an embodiment, the moveable member (30) is driven by an external magnetic force optionally using a gearbox (80), to convert the rotational movement of the external magnetic force into longitudinal movement of the moveable member (30) and the middle bone (35). According to an embodiment, the external force used to move the moveable member (30) may be applied from outside or externally from a patient's body and/or body part without breaking the skin or soft tissue.

According to an embodiment, the external actuator may include, but are not limited to rare earth magnets and/or electromagnets and may be arrayed around the extremity housing the bone segment to be moved. For example, with respect to an internal bone transport (100) located within the femur of a patient's leg, the magnetic material (90) of the external actuator may be arrayed around a section in an amount and location that may be used to rotate the internal rod (50) from outside the leg, preferably about 30% to about 40% of the leg's circumference. The external actuator would then be activated to produce the magnetic field to rotate the magnetic material (90) housed within the external rod (40). According to an embodiment, the external actuator may be located on one side of the extremity to avoid possible interference of the magnetic field.

Once the bone is of sufficient length and the middle bone (35) is growing towards both the first bone (25) and second bone (45), the internal bone transport (100) may be left in place to allow for complete bone healing. Upon completion of the healing process the internal bone transport (100) will be substantially or entirely housed within the bone and may be left within the intramedullary space thereby not requiring an additional surgery or may be removed. However, if removal of the internal bone transport (100) is desired, it may be removed through any surgical procedure known in the art and/or by any methods known in the art for removal of intramedullary rods and/or devices.

If not otherwise stated herein, it may be assumed that all components and/or processes described heretofore may, if appropriate, be considered to be useable with or interchangeable with similar components and/or processes disclosed in the following embodiments, unless an express indication is made to the contrary. For example, the internal bone transport device (200) discussed below may have coatings, or be formed with dimensions or from materials discussed above.

Figure 7:
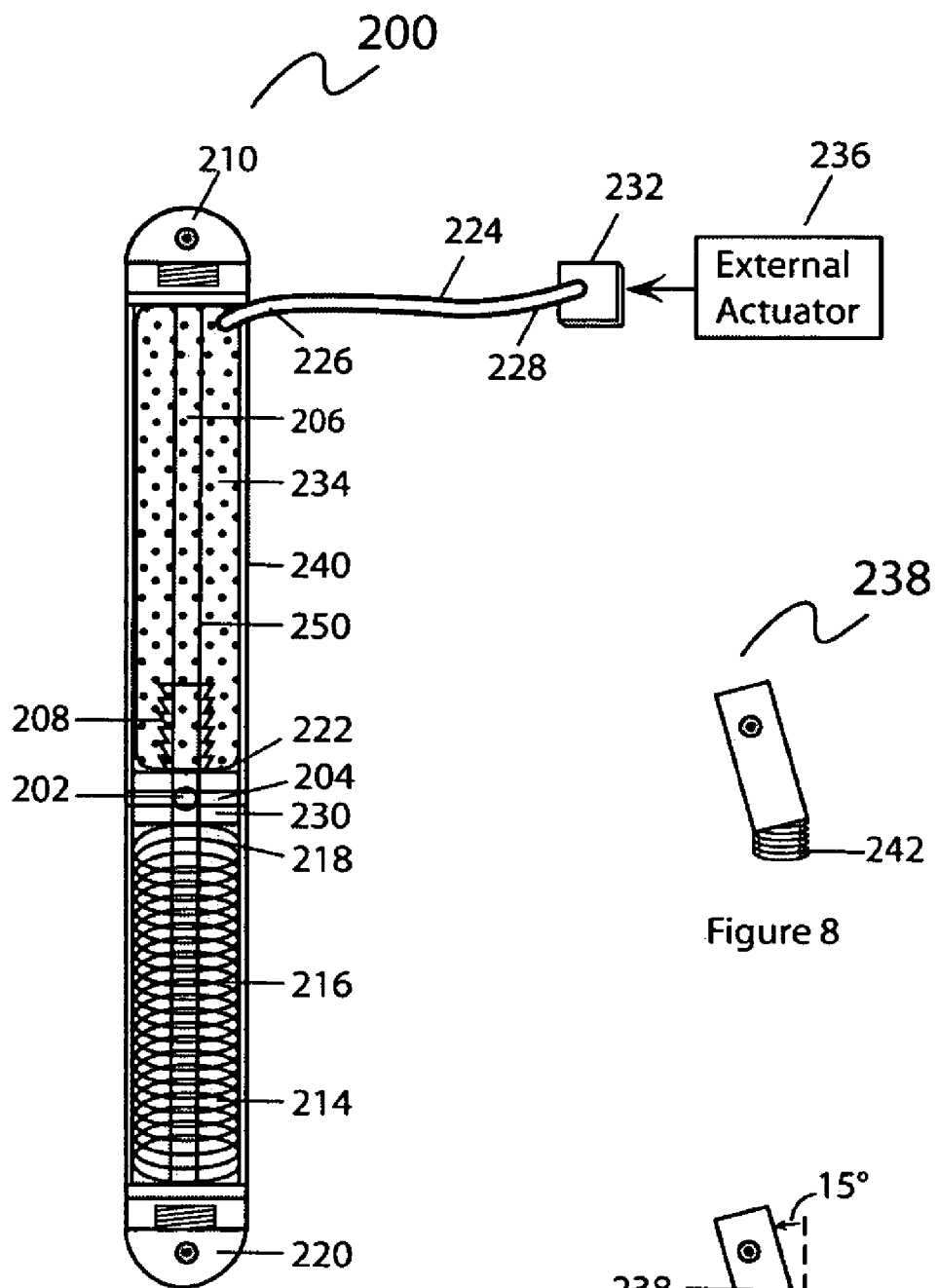
FIG. 7 is a schematic view of an embodiment of an internal bone transport device illustrating a fluid actuator in combination with a compression spring.

According to an embodiment, referring to FIG. 7, the internal bone transport device (200) has a hydraulic or fluid actuator in combination with a compression or torsional spring instead of a magnetic actuator. As in the previously described embodiments, the internal bone transport device (200) of the fluid actuator embodiment has a substantially fixed length external rod (240) with a first end (210) and a second end (220), each of which may be coupled, attached, or affixed to a different bone as described above. The internal bone transport (200) has at least one moveable member (230) having a central guide hole (202) coupled for movement along the internal rod (250). The moveable member (230) is coupled to a bone, for example, by a pair of interlocking screws (204), and is movable along the length of the external rod (240). The internal rod (250) is housed within the external rod (240) and is fixedly attached at each end to the first end (210) and second end (220) of the external rod (240). The internal rod (250) is preferably secured within the hollow of the external rod (240) such that the internal rod (250) is incapable of being rotated. The internal rod (250) preferably has etched markings (206) at 6 cm increments that may be seen by x-ray or other means. The internal rod (250) preferably has ratcheted teeth (208) cooperating with corresponding grooves (212) in the guide hole (202) of the moveable member (230) to allow only one-directional movement of the moveable member (230). A first end (214) of a compression or torsional spring (216) is attached, or affixed, for example by welding, to one of the first end (210) and second end (220) of the external rod (240), while the second end (218) of the compression spring (216) is attached, or affixed, for example by welding, to the moveable member (230). The compression spring (216) is tightly wound under compression thereby biasing the moveable member (230). The compression spring (216) is expandable at least 8 cm. The compression spring (216) is preferably formed from stainless steel and may be formed from any other suitable material such as of aluminum, titanium, or any other material suitable for implant devices. The compression spring (216) is preferably a helical spring but could be any appropriate geometric shape.

A variable volume fluid container such as a sealed bladder (222) is positioned between the other end of the external rod (240) and the moveable member (230). The sealed bladder (222) is preferably formed from silicone may be formed from any other suitable material such as polyelthelene or polytetrafluoroethylene. A flexible conduit (224) has a first end (226) fluidly coupled to the fluid container (222), while the second end (228) is coupled to a one-way valve (232) for selectively permitting fluid communication from the flexible conduit (224) into the body. The fluid container (222) and flexible conduit (224) are filled with a biocompatible fluid (234) such as saline or any other viscous biocompatible fluid. An external actuator (236) is positioned outside the device and may be positioned outside the body operable to control the one-way valve (232). The external actuator (236) is preferably a remote control device such as a magnetic, electromagnetic, radio frequency, and mixtures thereof controlled device. The external actuator (236) may also be a syringe or suitable device. Movement of the moveable member (230) is caused by the external actuator (236) opening the one-way valve (232) to allow fluid (234) to escape the variable-volume fluid container (222) and flexible conduit (224) into the body. This decreases the volume of fluid in the fluid container (222), thus, allowing the compression spring (216) to apply a force against the moveable member (230) on the side of the moveable member (230) opposite to the fluid container (222), thereby causing the moveable member (230) to move in a substantially lengthwise direction within the external rod (240). The one-way valve may be positioned close to the skin surface such that a syringe or other suitable device may be inserted to withdraw fluid.

According to an embodiment, the internal bone transport device (200) is operable to transport in a position oriented 180° from the one illustrated in FIG. 7 such that the transport is capable of both "top to bottom" and "bottom to top" transports. As discussed above, the external rod may have any diameter suitable for implantation. For example, an external rod for a femur may have an external diameter between about 12.5 and about 13 mm; and for a tibia, preferably 10 mm. The internal rod preferably has an external diameter of 2 mm.

Figure 10:
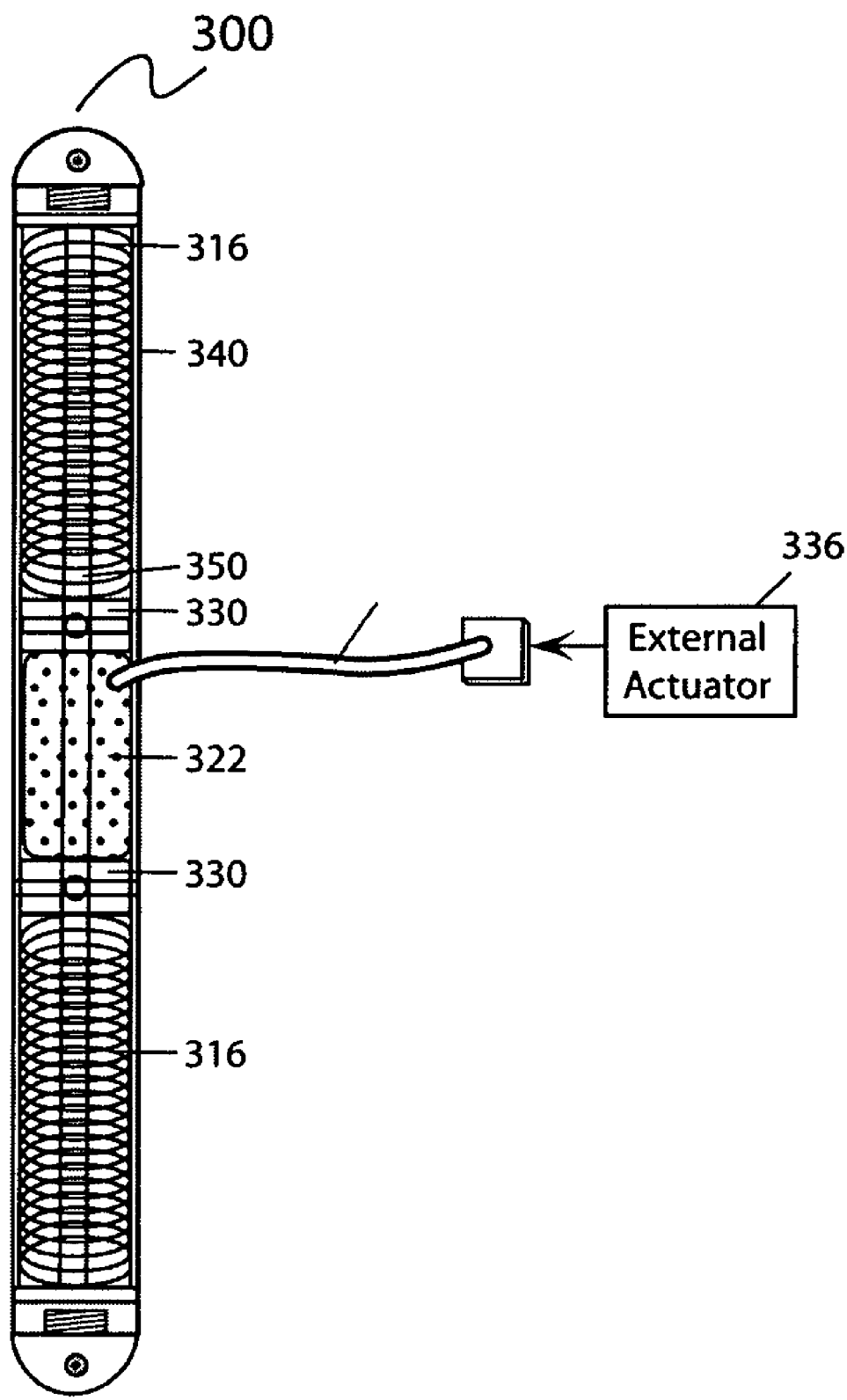
FIG. 10 is a schematic view of an embodiment of an internal bone transport device illustrating a fluid actuator in combination with a pair of compression springs for dual transport of a pair of bone segments.

According to an embodiment of the invention, referring to FIG. 10, an internal bone transport device (300) has a variable volume fluid container such as a sealed bladder (322) positioned between a pair of moveable members (330). As discussed above, each moveable member (330) is coupled to a bone segment and is movable along the length of the external rod (340). The device further includes a pair of compression springs (316) such that each spring is attached, or affixed, at one end to a moveable member (330) and at the other end to an end of the external rod (340). Upon actuation by an actuator (336), fluid is released from the variable-volume fluid container (322) thus, allowing the compression springs (316) to expand. The expansion of the compression springs (316) transports each moveable member (330) along the internal rod (350) towards the other moveable member (330). Thus, a pair of bone segments is able to be transported at the same time.

Figure 8:
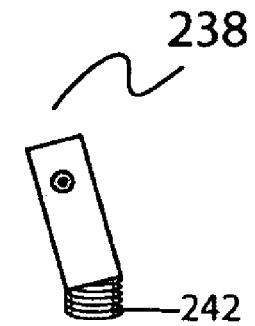
FIG. 8 is a schematic view of an embodiment of an adaptor piece to accommodate the proximal tibial curve.
Figure 9:
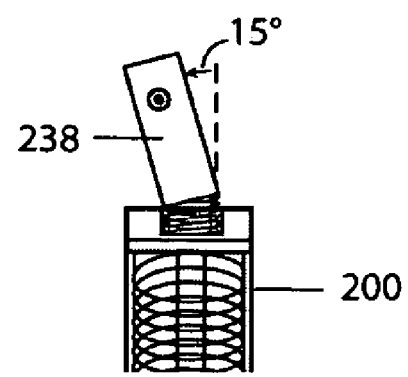
FIG. 9 a schematic view of the adaptor piece of FIG. 8 attached to an internal bone transport device.

According to an embodiment of the invention, referring to FIGS. 8 and 9, the internal bone transport device may include an adaptor piece (238) to provide a bend or curve to the external rod (240) in order to accommodate the proximal tibial curve and for ease of insertion. The adaptor piece (238) has an externally-threaded end (242) for attachment to a corresponding internally-threaded end (244) located on one of the ends of the external rod (240). The adaptor piece is angled at 15° from a vertical axis to accommodate the proximal tibial curve.

Although the present invention has been described in terms of specific embodiments, changes and modifications can be carried out without departing from the scope of the invention which is intended to be limited only by the scope of the claims.

What is claimed is:

1. An internal bone transport device, comprising:
 a substantially fixed length rod having a first end and a second end;
  wherein the first end of the substantially fixed length rod is configured to be coupled with a first portion of a bone to be lengthened and the second end is configured to be coupled with a second portion of the bone to be lengthened; and
 at least one moveable member placed between the first end and the second end of the substantially fixed length rod, wherein the moveable member is capable of moving substantially parallel to an axis which contains both the first end and the second end;
wherein the moveable member is configured to be coupled with a third portion of the bone to be lengthened;
a variable volume fluid container disposed between one of the first end and the second end of the substantially fixed length rod and the moveable member;
a compression spring disposed between the other of the first end and the second end of the substantially fixed length rod and the moveable member;
wherein the variable volume fluid container contains fluid;
a one-way valve, wherein the one-way valve allows fluid to be decreased in the variable volume fluid container;
wherein upon the decrease of at least a portion of the fluid from the variable volume fluid container, the compression spring expands to move the moveable member.

2. The device of claim 1, further comprising a flexible conduit having a first end and a second end, wherein the first end of the flexible conduit is in fluid communication with the variable volume fluid container.

3. The device of claim 2, further comprising a one-way valve in fluid communication with the second end of the flexible conduit, wherein removal of fluid from the one-way valve removes fluid from the variable volume fluid container.

4. The device of claim 3, wherein the one-way valve is actuated by an external actuator located outside the body.

5. The device of claim 4, wherein the external actuator is operable using a force selected from the group consisting of: magnetic, electromagnetic, radio frequency, and mixtures thereof.

6. The device of claim 1, wherein the variable volume fluid container is a flexible bladder.

7. The device of claim 6, wherein the flexible bladder is formed from silicone.

8. The device of claim 1, wherein the substantially fixed length rod comprises one or more materials selected from the group consisting of: titanium, medical grade titanium, stainless steel, surgical grade stainless steel, and cobalt chromium.

9. The device of claim 1, wherein the moveable member comprises one or more materials selected from the group consisting of: titanium, medical grade titanium, stainless steel, surgical grade stainless steel, and cobalt chromium.

10. The device of claim 1, further comprising a coating of one or more selected from the group consisting of: an antibiotic, silver, a bone morphogenic protein, parylene, and an inert substance that prevents corrosion, wherein the coating is applied to at least a portion of the device.

11. The device of claim 1, further comprising a coating of one or more selected from the group consisting of: an antibiotic, silver, a bone morphogenic protein, parylene, and an inert substance that prevents corrosion, wherein the coating is applied to at least a portion of the bone.

12. The device of claim 1, further comprising an angled adaptor for attachment to one of the first end and the second end of the substantially fixed length rod.

13. An internal bone transport device, comprising:
a substantially fixed length rod having a first end and a second end;
wherein the first end of the substantially fixed length rod is configured to be coupled with a first portion of a bone to be lengthened and the second end is configured to be coupled with a second portion of the bone to be lengthened; and
a first moveable member placed between the first end and the second end of the substantially fixed length rod, wherein the moveable member is capable of moving substantially parallel to an axis which contains both the first end and the second end;
wherein the first moveable member is configured to be coupled with a third portion of the bone to be lengthened;
a second moveable member placed between the first end and the second end of the substantially fixed length rod, wherein the second moveable member is capable of moving substantially parallel to an axis which contains both the first end and the second end;
wherein the second moveable member is configured to be coupled with a fourth portion of the bone to be lengthened;
a variable volume fluid container disposed between one of the first end moveable member and the second moveable member;
a first compression spring disposed between the first end of the substantially fixed length rod and the first moveable member;
a second compression spring disposed between the second end of the substantially fixed length rod and the second moveable member;
wherein the variable volume fluid container contains fluid;
a one-way valve, wherein the one-way valve allows fluid to be decreased in the variable volume fluid container:
wherein upon the decrease of at least a portion of the fluid from the variable volume fluid container, the first compression spring and second compression spring expand to move the first moveable member and the second moveable member towards one another.

* * * * *